US006437003B1

(12) United States Patent
Roullet et al.

(10) Patent No.: US 6,437,003 B1
(45) Date of Patent: Aug. 20, 2002

(54) USE OF RETINOIDS TO TREAT HIGH BLOOD PRESSURE AND OTHER CARDIOVASCULAR DISEASE

(76) Inventors: Jean-Baptiste Roullet, 4124 Tunnelwood St., Portland, OR (US) 97221; David A McCarron, 2605 SW. Buena Vista St., Portland, OR (US) 97201

(*) Notice: Subject to any disclaimer, the term of this patent is extended or adjusted under 35 U.S.C. 154(b) by 0 days.

(21) Appl. No.: 09/325,241

(22) Filed: Jun. 3, 1999

Related U.S. Application Data

(63) Continuation of application No. 08/961,627, filed on Oct. 31, 1997, now abandoned.

(51) Int. Cl.$^7$ ................................................ A61K 31/07
(52) U.S. Cl. ..................................................... 514/725
(58) Field of Search ......................................... 514/725

(56) References Cited

U.S. PATENT DOCUMENTS

| | | |
|---|---|---|
| 4,386,095 A | 5/1983 | Gibson et al. |
| 4,694,085 A | 9/1987 | Losel et al. |
| 5,037,821 A | 8/1991 | Horovitz |
| 5,350,771 A | 9/1994 | Pang et al. |
| 5,435,998 A | 7/1995 | Abelson |
| 5,576,349 A | 11/1996 | Leaf et al. |
| 5,594,015 A | 1/1997 | Kurtz et al. |
| 5,723,666 A * | 3/1998 | Vuligonda et al. .......... 564/253 |
| 5,728,739 A | 3/1998 | Ailhaud et al. |
| 5,770,383 A | 6/1998 | Hwang et al. |

OTHER PUBLICATIONS

Klaus (1990) "Structure of Retinoids," *Methods in Enzymology*, Academic Press 89:3–14.
Dawson et al. (1990) "Synthetic Retinoic Acid Analogs," *Methods in Enzymology*, Academic Press 89:15–42.
Sani et al. (1990) "Structural Characteristics of Synthetic Retinoids," *Methods in Enzymology*, Academic Press 89:43–59.
Woo et al. (1989) *J. Clin. Pathol.* 42:1241–1245.
Horwitt et al. (1975) *Am. J. of Clin. Nutrition* 23:403–412.
Ripley et al. (1996) *Alcohol & Alcoholism* 31:347–357.
Desai et al. (1995) *Indian J. Exp. Biol.* 33(12):931–934.
Straub et al. (1996) *Brain Res.* 733(2):307–311.
Momiyama et al. (1995) *Eur. J. Pharmacol.* 280(2): 119–123.
Straub et al. (1994) *Brain Res.* 658(1–2):119–126.
Speckmann et al. (1993) *Neuropsychobiol.* 27(3):122–126.
Katz et al. (1987) *J. Clin. Pharmacol.* 27:825–834.
Ritchie et al. (1993) *Int. Arch. Allerg. Immunol.* 100:274–282.
Pierce et al. (1989) *Endocrinology* 125(2):730–735.
Bhatnager et al. (1995) *Exp. Eye Res.* 61(3):303–310.
Hebuterne et al. (1996) *J. Lipid Res.* 37:482–492.
Tanaka (1996) *Development. Biol.* 17S:239–247.
Scita et al. (1993) *Methods in Enzymol.* 214:21–32.
Fleckenstein et al. (1967) *Z. Kreislaufforsch* 56:716–744.
Hans et al. (1994) *Acta Anesthesiologica Belgica* 45(4):175–178.
Dodd et al. (1993) *Drug Design & Discovery* 10:65–75.
Ziari et al. (1996) *Amer. J. Perinatology* 13(5) 287–91.

\* cited by examiner

*Primary Examiner*—Theodore J. Criares

(57) ABSTRACT

This invention provides methods of treating a disease in a mammal where the disease is characterized by a symptom ameliorated by inhibition of cellular calcium influx. The methods involve administering to the mammal an effective amount of a retinoid and a pharmacologically acceptable excipient.

6 Claims, 7 Drawing Sheets

USE OF RETINOIDS TO TREAT HIGH BLOOD PRESSURE AND OTHER CARDIOVASCULAR DISEASE

CROSS-REFERENCE TO RELATED INVENTIONS

This application is a continuation of and claims priority from application Ser. No. 08/961,627, filed Oct. 31, 1997, the disclosur of which is incorporated herein by reference.

STATEMENT AS TO RIGHTS TO INVENTIONS MADE UNDER FEDERALLY SPONSORED RESEARCH AND DEVELOPMENT

[Not Applicable]

BACKGROUND OF THE INVENTION

Calcium channel blockers are a relatively recently discovered class of compounds which possess a wide spectrum of properties useful in the treatment of cardiovascular, cerebrovascular, intraocular, and other disorders. Calcium channel blockers were initially identified as a method for the control of hypertension (Fleckenstein et al. (1967) *Z. Kreislaufforsch*, 56: 716), and are routinely used in the control of hypertension and other disorders. In particular, calcium blockers have shown some useful therapeutic properties in the treatment of classic exertional angina, vasospastic angina, angina pectoris, acute myocardial infarction, cardiac arrhythmias, systemic arterial hypertension, pulmonary arterial hypertension, and cardiomyopathies. In addition, calcium channel blockers have shown therapeutic properties in the treatment of various cerebrovascular disorders, including but not limited to migraine headaches, and convulsive epilepsy.

Several structural classes of compounds are known which exhibit calcium channel blocking utility and have been used as therapeutics in a variety of contexts. The three major classes include dihydropynidines (e.g., nifedipine, felodipine, isradipine, and amlodipine), the benzothiazepines (e.g., diltiazem), and the phenylalkylamines (e.g., verapamil). Three calcium channel blockers are currently of primary clinical significance in the United States, verapamil, nifedipine and diltiazem. All three achieve their antihypertensive effect by inhibiting the entry of calcium ions into vascular smooth muscle. The ultimate effect is vasodilation. These calcium blockers are, however, contraindicated in various circumstances (e.g., where there is impaired left ventricular function). Thus, there is a need for other calcium blocking agents.

SUMMARY OF THE INVENTION

The present identifies previously unknown calcium channel blocking properties of retinoids, in particular retinol, and provides methods of treating pathological conditions characterized by and ameliorated by inhibition of cellular calcium influx using retinoids. Retinoids (e.g., vitamin A and analogues) are lipid-soluble and can therefore achieve extensive distribution within body tissues. They are also rapidly absorbed after oral or intravenous administration and, because of their affinity for fatty tissues, provide a reservoir that maintains elevated retinoid levels for some time after administration. In addition, the physiological tolerance for many retinoids (e.g., vitamin A) has been repeatedly demonstrated and well characterized.

Thus, in one embodiment, this invention provides a method of treating a disease in a mammal where the said disease is characterized by a symptom ameliorated by inhibition of cellular calcium influx. The method typically involves administering to the mammal an effective amount of a retinoid and a pharmacologically acceptable excipient. It will be appreciated that while a major application of the method involves treatment of humans, the methods are not so limited and treatment of virtually any mammal is contemplated. In a particularly preferred embodiment, the mammal is selected from the group of mammals having a disease characterized by one or more symptoms responsive to (ameliorated by) inhibition of calcium influx into a cell.

It is primarily contemplated that the methods will be practiced for the primary purpose of treatment of a condition one or more symptoms of which are responsive to calcium channel blockage. The methods do not contemplate administration of a retinoid for the purpose of diet supplementation. Thus, the retinoid is not a dietary supplement. The methods may thus additionally involve the step of assaying for retinoid-mediated amelioration of a symptom of a disease state. Typically the symptom will be one expected to be responsive to a calcium channel blocker. Similarly, the methods may additionally involve identifying a subject mammal (e.g., a patient) having a disease state expected to prove responsive to a calcium channel blocker.

The methods can be used to treat a wide variety of diseases including, but not limited to essential hypertension, hypertension associated with end stage renal failure, hypertension associated with pregnancy (preeclampsia), salt sensitivity hypertension, type II diabetes hypertension, hypertension associated with alcohol abuse, obesity associated hypertension, systolic hypertension in elderly, asthma, allergies, migraine headache, gastrointestinal motility disorders, Alzheimer's disease, senile dementia, angina pectoris, premature labor, cerebrovascular diseases, and convulsive epilepsy. The methods, however, are particularly well suited for treatment of essential hypertension and intra-ocular hypertension.

Any of a variety of retinoids are suitable. Particularly preferred retinoids include retinoic acid and retinol, with retinol being most preferred. The pharmacologically acceptable excipient is preferably lipid compatible. A most preferred retinoid inhibits cellular influx of calcium through inhibition of voltage gated channels in particular L-type voltage-gated calcium channels.

In another embodiment, this invention provides a method of treating a disorder which is responsive to the partial or complete blockade of calcium channels of the central nervous system of a living mammal. Again the method involves administering to such a living mammal in need thereof, a therapeutically effective amount of a retinoid as described herein. The disorder can include stroke, anoxia, ischemia, migraine or epilepsy, psychosis, Parkinsonism, depression, or any other convulsive disorder. In still another embodiment, the method involves treating the degenerative changes, connected with stroke, anoxia, ischemia, migraine, Parkinsonism, epilepsy or any other convulsive disorder, responsive to the partial or complete blockade of calcium channels of the central nervous system of a living animal body, by administering to a living animal body in need thereof a therapeutically-effective amount of a retinoid as described herein.

In still another embodiment, this invention provides methods of inhibiting calcium influx into a mammalian cell. The methods involve contacting the cell with a retinoid. The retinoid is present in an amount sufficient to inhibit, partially or fully, a calcium channel, more preferably a L-type voltage-gated calcium channel. Virtually any retinoid is suitable, however in a preferred embodiment, the retinoid is retinol or retinoic acid, more preferably retinol. The cell can be virtually any mammalian cell, however preferred cells include muscle cells, more preferably smooth muscle cells, most preferably vascular muscle cells, or cells of the nervous system, more preferably cells of the central nervous system. The cell can be in vivo or in vitro.

In yet another embodiment this invention provides kits for the treatment of a disease in a mammal where the disease is characterized by a symptom ameliorated by inhibition of cellular calcium influx. The kits typically comprising a container containing a retinoid in a pharmaceutically acceptable excipient and instructional materials teaching the use of a retinoid to inhibit calcium influx in the treatment of a disease characterized by a symptom ameliorated by inhibition of cellular calcium influx. The disease includes, but is not limited to any essential hypertension, hypertension associated with end stage renal failure, hypertension associated with pregnancy (preeclampsia), salt sensitivity hypertension, type II diabetes hypertension, hypertension associated with alcohol abuse, obesity associated hypertension, systolic hypertension in elderly, asthma, allergies, migraine headache, gastrointestinal motility disorders, Alzheimer's disease, senile dementia, angina pectoris, premature labor, cerebrovascular diseases, and convulsive epilepsy. Any of the retinoids described herein is suitable and a preferred retinoid is retinol.

DEFINITIONS

The terms "treating" and "treatment" refer to any treatment of a disease in a mammal, particularly a human, and generally include: (i) preventing the disease from occurring in a subject which may be predisposed to the disease but has not yet been diagnosed as having it; (ii) inhibiting the disease, i.e., arresting its development; or (iii) relieving the disease, i.e., causing regression of the disease. Treating also refers to providing a beneficial alteration in one or more of the symptoms of a disease state or reducing or eliminating the disease state itself. It will be appreciated that a beneficial alteration can include transitory or permanent reduction or elimination of the symptom. It will also be appreciated that "treating" can also involve a reduction in actual adverse consequences or a reduction in the likelihood of adverse consequences of a pathological state. Thus treatment as used herein can also refer to prophylaxis. For example, treatment of hypertension can involve actual reduction or systolic or diastolic blood pressure. Alternatively treatment can reflect a reduction in the likelihood of stroke, e.g., where the reduction in likelihood is brought about by the reduction of blood pressure.

The term effective amount is intended to mean the amount of a drug, or multidrug therapeutic, which achieves a positive outcome on one or more symptoms of a disease state or which acts prophylactically to reduce the likelihood of one or more pathological symptoms or consequences of a disease state. Thus, for example, an effective amount of a drug for the treatment of hypertension can refer to an amount of a drug sufficient to transiently or permanently reduce blood pressure (e.g., diastolic pressure) or to reduce the likelihood of the onset of a stroke.

A calcium channel is a passive transport mechanism by which calcium ions move down their electrochemical gradient. In all cells, calcium concentration is low inside the cell (e.g., $10^{-7}$ M) and high in the extracellular medium (e.g., $10^{-3}$ M) and so a calcium channel allows calcium to go into the cell. By contrast, outward calcium transport takes place via "a calcium pump," an entirely different mechanism which transports calcium against a concentration gradient (from the low concentration inside to the high concentration outside). An ion pump is therefore an active membrane structure, usually an enzyme (e.g., sodium ATPase) which requires energy (ATP: adenosine triphosphate) to carry ions across the membrane.

The term "administering" when used in the context of "administering to a mammal" refers to delivering the drugs in question to a subject organism (e.g., mammal). Administration can be topical, intraperitoneal, subdermal, etc., as described herein.

The term "pharmacologically acceptable excipient" or "pharmaceutically acceptable excipient" refers to a diluent or excipient suitable for administration to an organism. Administration can be topical or systemic, directed to particular tissues, organs or cells. The excipient is-essentially a carrier agent to facilitate administration of the active ingredient (e.g., retinoid). The excipient may contain auxiliary substances as required to approximate physiological conditions, such as pH adjusting and buffering agents, tonicity adjusting agents, wetting agents, solubilizers, emulsifiers and the like.

The term dietary supplement is used to distinguish a compound taken to augment or replace an ingredient otherwise diminished or absent in a diet from a compound taken to specifically treat a particular disease/pathology. Thus, for example, a vitamin can be taken as a dietary supplement to ensure adequate dietary quantities of that vitamin or to supplement dietary defficiencies. Such a dietary supplement is, however, generally not taken to treat a specific disease or pathological state.

The term "contacting a cell" when referring to contacting with a drug is used herein to refer to contacting in a manner such that the drug is internalized into the cell or into specific cellular components (e.g., plasma membrane). Where the drug is lipophilic or complexed with a lipid (e.g., a cationic lipid) simple contacting will result in transport (active and/or diffusive) into the cell. Alternatively the drug may itself be actively transported into the cell or may be administered with a carrier composition that is actively transported into the cell.

The terms "optional" and "optionally" mean that the subsequently described event or circumstance may or may not occur, and that the description includes instances where said event or circumstance occurs and instances in which it does not. For example, the phrase "optional pharmaceutical excipients" indicates that a composition or dosage form so described may or may not include pharmaceutical excipients other than those specifically stated to be present, and that the formulation or dosage form so described includes instances in which optional excipients are present and instances in which they are not.

The term "pharmaceutically acceptable acid addition salts" refers to salts of the subject compounds which possess the desired pharmacological activity and which are neither biologically nor otherwise undesirable. Thus the retinoids of this invention may be administered in combination with pharmaceutically acceptable acid addition salts. These salts are formed with inorganic acids such as hydrochloric acid, hydrobromic acid, sulfuric acid, nitric acid or phosphoric acid and the like; or organic acids such as acetic acid, propionic acid, glycolic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid and the like.

The terms "fast release" and "conventional release" refer to orally administered calcium channel blocker compositions that are substantially completely dissolved and absorbed in the stomach or upper gastrointestinal tract.

The terms "long acting" and "sustained release" when used in reference to oral formulations, refer to calcium channel blocker compositions that are slowly and continuously dissolved and absorbed in the stomach and gastrointestinal tract over a period of at least two hours. Preferred long acting compositions and dosage forms exhibit plasma concentration profiles suitable for once daily administration of the dosage form.

The term "lipid compatible" when used with respect to a diluent or excipient indicates that the diluent or excipeint is capable of solubilizing, emulsifying, or suspending a lipophilic compound (e.g,. a retinoid).

DETAILED DESCRIPTION

Figure 1:
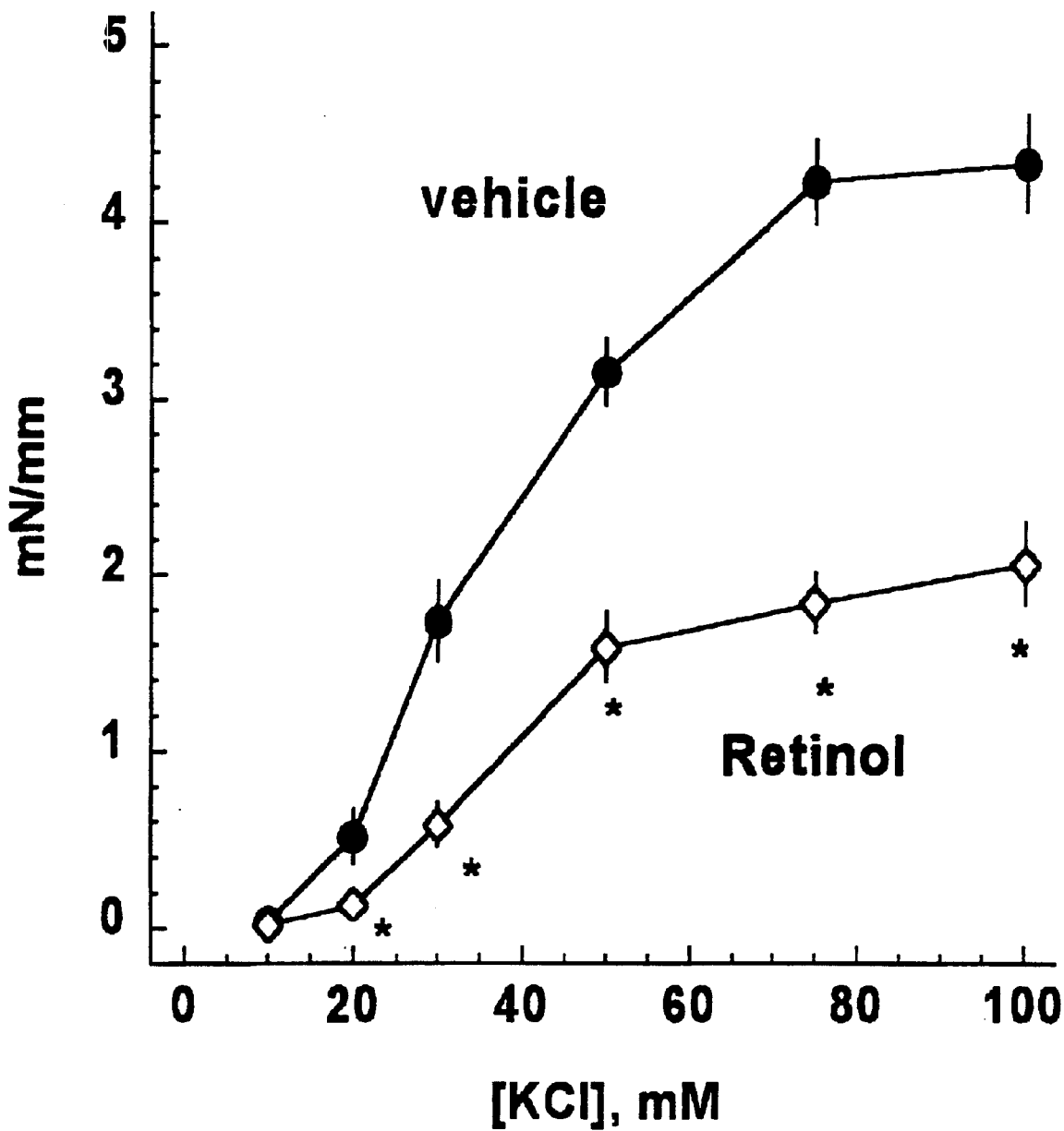
FIG. 1 is a plot showing the inhibitory effect of retinol on vascular contractions induced by KCl.

This invention relates to therapeutically active compounds effective in inhibiting calcium influx into a cell. In particular, it was a discovery of this invention that retinoids and especially retinol, act as potent calcium channel blockers. The retinoids act generally to reduce or eliminate calcium ion ($Ca^{2+}$) influx into mammalian cells. In particular, the retinoids are effective to inhibit calcium influx through slow voltage-gated calcium channels, more specifically through L-type voltage-gated calcium channels.

Accordingly, it was also a discovery of this invention that retinoids are effective in the treatment of mammalian diseases characterized by one or more symptoms ameliorated by inhibition of cellular calcium influx. Such diseases include, but are not limited to various conditions generally referred to as hypertension, (e.g., essential hypertension, end stage renal hypertension), cerebrovascular disorders, and convulsive epilepsy.

Generally the methods of this invention involve administering to a mammal in need of such treatment, a therapeutically effective dose of a retinoid. The administered retinoid contacts target cells (e.g., smooth muscle cells) where it blocks calcium channels inhibiting calcium influx and thereby mitigating or eliminating one or more symptoms of a disorder. The retinoid is preferably administered in a pharmacological acceptable excipient. It will be appreciated that such treatments can be applied to human patients, or to other mammals (e.g., murines, porcines, largomorphs, bovines, equines, ungulates, primates, and the like). This invention thus provides methods of treatment effective both in the human medical context, in veterinary medicine, and in laboratory research.

I. Use of Retinoids to Treat Diseases.

The pharmaceutical compositions and dosage forms of the invention may be used for treating a wide variety of disease states which involve one or more forms of cardiovascular, cerebrovascular, and intraocular dysfunction. The retinoids of this invention generally possess a broad spectrum of cardiovascular and cerebrovascular activities including anti-anginal and antihypertensive properties. The invention compositions can therefore be beneficially used in treating cardiovascular disorders, cerebrovascular disorders, and certain intraocular disorders in patients who are susceptible to calcium ion entry blockade.

A) HvDertension.

In one embodiment, this invention provides a safe, highly effective method for treating severe hypertension and may offer an alternative to side effects associated with other antihypertensive drugs (e.g., nitrendipine). The present invention relies on the calcium channel blocking activity of retinoids, for example, for treatment or prevention of hypertension, while simultaneously reducing many of the undesirable side effects (e.g., headache, nausia) associated with other known anti-hypertensive drugs.

In particular, the retinoids of this invention are useful in the treatment of essential hypertension and/or various secondary hypertensive conditions (e.g., end stage renal hypertension, pregnancy associated hypertension such as preeclampsia, hypertension associated with type II diabetes, salt sensitivity hypertension, hypertension associated with alcohol abuse, hypertension associated with obesity, and systolic hypertension in the elderly).

Treatment of hypertension using retinoids typically involves first diagnosing the hypertensive condition and whether treatment with a calcium blocker is appropriate; administration of a retinoid and/or other drug(s) in a therapeutic regimen, monitoring response of the subject, and, if necessary, altering/optimizing dosage/treatment regimen.

Methods of diagnosing essential or secondary hypertension are well known to those of skill in the art (see, e.g., Isselbacher et al. (1994) *Harrison's Principles of Internal Medicine*, 13$^{th}$ Ed., McGraw-Hill, Inc., New York). Physical examination and laboratory tests are directed at (1) uncovering correctable secondary forms of hypertension; (2) establishing a pretreatment baseline, (3) assessing factors which may influence the type or therapy or which may be adversely modified by therapy, (4) determining if target organ damage is present and (5) determining whether other risk factors for the development or arteriosclerotic cardiovascular diseases are present.

In the event treatment with calcium blockers is indicated, the retinoids of this invention can be administered to the subject organism (e.g., patient) alone or in combination with other medicaments (e.g., other anti-hypertensives such as diuretics, antiadrenergic agents, angiotensin-converting enzyme (ACE) inhibitors, other calcium channel antagonists (e.g., nifedipine, amlodipine, verapamil, diltiazem, etc.), or other pharmacological agents) as described below. The patient will be monitored and evaluated according to standard methods in the art and dosages adjusted accordingly.

In this context, it will be noted that while calcium channel antagonists are useful in the treatment of angina pectoris, because of their negative inotropic actions they should be used with caution in hypertensive patients.

In one method-the retinoid can be administered to an individual suffering from hypertension. For example, a composition comprising a retinol and a pharmaceutically acceptable excipient is administered therapeutically to an individual to reduce or ameliorate hypertension. In another embodiment, a retinoid can be administered prophylactically to reduce the probability of occurrence of hypertension or to mitigate and/or prevent the onset of hypertension associated pathologies (e.g., stroke, kidney failure, etc.).

B) Angina Pectoris.

Angina Pectoris results from the narrowing of the coronary arteries and subsequent reduction in blood supply to the myocardium. Total obstruction of these arteries lead to myocardial infarction. Typical treatment of angina pectoris include the use of potent vasodilators such as nitrite derivative as well as that of classical $Ca^{2+}$ channel blockers.

The retinoids of this invention which have demonstrated powerful vasodilatory properties, will therefore be used in the treatment of angina pectoris and myocardial infarction.

C) Cerebrovascular and Neurological Disorders.

It is well known that an accumulation of calcium occurs in brain cells after anoxia, ischemia, ischemic or hemorrhagic stroke, and vascular dementia. An uncontrolled high concentration of calcium in the cells of the central nervous system is known to cause most of the degenerative changes connected with the above diseases.

Therefore compounds which can reduce calcium accumulation in brain cells by directly blocking calcium uptake, will be useful in the treatment of anoxia, ischemia, ischemic or hemorrhagic stroke, vascular dementia, and in the prevention of the degenerative changes connected with the same.

It is also established that spasms in the cerebral vasculature may be responsible for the onset of migraines or migraine headaches. Compounds which can reduce calcium influx in the cerebral vasculature also reduce vasospasm.

Therefore compounds which can block the calcium channels of the cerebral vasculature will be useful in the treatment of migraines and migraine headaches.

It is also established that calcium is an important second messenger which plays a role in the regulation of neurotransmitter release and action. Neurotransmitters include but are not limited to aspartate, glutamate, GABA, glycine, dopamine, serotonin and noradrenaline. It is also established that voltage-gated calcium channels, including L-, N-, and/or P-types calcium channels, as well as other types of calcium channels participate in the signaling role of calcium in brain cells. Compounds, partially or completely, blocking one or more of the brain calcium channels will indirectly and powerfully prevent hyperactivity of the brain and brain toxicity manifestations due to exaggerated neurotransmitter release or action. Therefore, blockers of L-, N-, and/or P-types calcium channels, as well as other types of calcium channels are expected to be useful in the treatment of psychosis, Parkinsonism, depression, epilepsy and other convulsive disorders.

It is well established that ethanol withdrawal is associated with hyperexcitability of central neurons and that the increased responsiveness demonstrated to excitatory amino acids (EAA) may contribute to the physical signs of ethanol withdrawal and to neurodegeneration. Although the mechanisms of neuronal hyperexcitation during ethanol withdrawal are not fully understood, there is considerable evidence to suggest that an increase in both neurotransmitter receptor activity and voltage-gated calcium channels may play an important role. In particular, dihydropyridines can significantly attenuate EAA- induced cytotoxicity in ethanol-withdrawn cells (Ruhe et al. (1994) *Alcohol & Alcoholism*, 2:217–221), and can prevent the development of ethanol dependence in the animal (Ripley et al. (1996) *Alcohol & Alcoholism*, 31:347–357).

Thus, retinoids could prevent alcohol dependence, attenuate withdrawal symptoms and reduce alcohol-induced neurodegeneration.

It is also established that $Ca^{2+}$ influx in brain cells are involved in epileptogenesis. Studies have shown that calcium channel blockers have anticonvulsant and antiepileptic properties by reducing neuron excitability (Desai et al. (1995) *Indian J Exp. Biol.* 33(12): 931–934; Straub H. et al. (1996) *Brain Res.* 733(2): 307–311; Momiyama et al. (1995) *Eur. J. Pharmacol.* 280(2): 119–123; Hans et al. (1994) *Acta Anesthesiologica Belgica*, 45(4): 175–178; Straub et al. (1994) *Brain Res.* 658(1–2): 119–126; Speckmann et al. (1993) *Neuropsychobiol.* 27(3): 122–126).

Therefore, the retinoids of this invention are expected to prove useful in the treatment of convulsive epilepsy and related diseases.

Thus, it is an object of the present invention to provide retinoid compositions and retinoid-based methods for partially or completely blocking neuronal or cerebrovascular L-type and/or N-type and/or P-type calcium channels, and/or other types of calcium channels in the treatment of the aforementioned cerebrovascular and neurological disorders. In one embodiment, the invention then, inter alia, comprises a method of treating a disorder, which is responsive to the partial or complete blockade of calcium channels of the central nervous system of a living animal body, including a human, which comprises administering to such a living animal body, including a human, in need thereof, a therapeutically-effective amount of a retinoid as described herein.

As with hypertension, treatment involves first diagnosing the disorder and determining whether treatment with a calcium blocker is appropriate; administration, if appropriate, of a retinoid and/or other drug(s) in a therapeutic regimen; monitoring response of the subject, and, if necessary, altering/optimizing dosage/treatment regimen. Methods of diagnosing cerebrovascular disorders are also well known to those of skill in the art (see, e.g., Harrison's supra.) as are methods of administering and optimizing calcium blocker treatment.

D) Loss of Cognitive Function.

It has been demonstrated on a number of occasions that treatment with calcium channel blockers appears to inhibit loss of congnitive finctions including memory, which are associated with different types of dementias. Thus, for example, Katz et al. (1987) *J. Clin. Pharnacol*, 27: 825–834, teach that nimodipine is useful in the treatment of dimensia. Similarly, Albizzati et al. (1987) *Drugs*, 33 Suppl. 2: 90–96, teach that when flunarizine was tested in patients with dementia, improvement was observed in neurological impariment, ischemia scores, Gottfries scale, and Hamilton depression scales. Qin et al. (1986) *Chung Kuo I Huseh Ko Hsueh Yuan Hsueh Pao*, 8: 366–370, disclose that nimodipine, nifedipine, and vincamine improve amnesia induced by anisodine and sodium nitrate in rats and mice. Similarly U.S. Pat. No. 4,386,095 discloses that certain diaminopyridines improve cognition, U.S. Pat. No. 4,694, 085 discloses that certain 5, 6-dihydropyrolo(2, 1-a) isoquinolines are calcium antagonists and nootropic agents, and U. K. patent Application 2,176,788A discloses that certain 2-halonicergoline compounds are calcium antagonists and improve cognitive action of the brain.

Moreover, it has been demonstrated that the combination of a calcium channel blocker with an angiotensin converting enzyme inhibitor (ACE inhibitor) if effective in inhibiting loss of cognitive functions (see, e.g., U.S. Pat. No. 5,037,821). Thus, in accordance with the present invention, a method is provided for inhibiting loss of cognitive functions such as memory, attention span, concentration and the ability to learn or for treating or delaying progression of Alzheimer's disease or other types of dementias in mammalian species. The methods involve treating the mammalian species (e.g., a human) with a retinoid calcium channel blocker alone or in combination with an angiotensin converting enzyme inhibitor (ACE inhibitor). In a preferred embodiment the retinoid and optionally the ACE inhibitor, is administered systemically (e.g., orally or parenterally) over a prolonged period to inhibit loss of cognitive function during such period. Where the calcium channel blocker is used with an ACE inhibitor, the retinoid will be employed in a weight ratio to ACE inhibitor in a range of about 0.02:1 to about 20:1 and preferably from about 0.4:1 to about 4:1.

E) Onthalmic diseases.

Glaucoma is an optical neuropathy associated with elevated intraocular pressures which are too high for normal finctions of the eye, and results in irreversible loss of visual function. It is estimated that glaucoma afflicts approximately two percent of the population over the age of forty years, and is therefore a serious health problem. Ocular hypertension, i.e. the condition of elevated intraocular pressure, which has not yet caused irreversible damage, is believed to represent the earliest phase of glaucoma.

Many therapeutic agents have been devised and discovered in the prior art for the treatment or amelioration of glaucoma and of the condition of increased intraocular pressure which precedes glaucoma.

Primary open angle glaucoma (POAG) is associated with a rise in intraocular pressure (IOP). This increase in IOP is believed to contribute to the loss of optic nerve function which ultimately leads to blindness. Reduction of IOP is therefore a crucial component in the management of POAG. Pharmacological protection of the optic nerve is also viewed as a means of reversing or preventing further damage of the optic nerve. In this respect, reduction of calcium-induced damage by using calcium channel blockers has been proposed as a strategy to manage glaucoma and its ultimate complication, blindness.

A related condition, low-tension glaucoma is an ophthalmic condition in which the symptoms and ophthalmic pathology, ie., loss of visual fields, loss of visual acuity and contrast sensitivity, cupping of the optic disk, etc., are present in the eye, but the intraocular pressure (IOP) is normal or only slightly elevated. It is distinguishable from primary open angle glaucoma, which is characterized by an elevated IOP. The etiology of the disease is not well understood and consequently there is no consensus as to a medicinal course of therapy. Nevertheless, conventional ophthalmic medications that lower the IOP have been used in an attempt to maintain the IOP as low as possible, even somewhat below the range usually considered as normal. Systemic drugs that increase the blood flow to the optic nerve head and/or retina have been found to have some effect in alleviating the loss of visual function in low-tension glaucoma and in primary open angle glaucoma. In particular, systemic, e.g., oral, administration of calcium channel blocking agents has been found to be of benefit in low-tension glaucoma.

Accordingly, in view of the discovery that retinoids act as effective calcium channel blocking agents, this invention provides methods of treating primary open angle glaucoma, and/or low-tension glaucoma by administration to the eye of a human or mammal so afflicted an amount of a retinoid (calcium channel blocking agent) effective to increase blood flow to the optic nerve head and/or retina, and to reduce calcium accumulation in the optic nerve.

In a particularly preferred embodiment, this treatment will be accomplished by topical administration to the eye of a human or mammal afflicted with a glaucoma (or possibly at risk for progression to glaucoma) a composition comprising an effective amount of a retinoid. Methods of treating glaucoma(s) using other calcium blockers (e.g., methods of determining dosage/treatment regimen and routes of administration) are well known to those of skill in the art (see, e.g., U.S. Pat. No: 5,435,998).

F) Other Conditions Mediated by Calcium Blockers.

Symptoms of a number of other conditions are known to be alleviated by treatment with calcium channel blockers. Such conditions include, but are not limited to diseases affecting or implicating smooth muscle cells from tissues other than the vascular tissue. These conditions can be treated by the application of retinoid-based calcium blockers as described herein.

In particular, it is well known that asthma and allergies are characterized by a stimulus-dependent bronchospasm leading to decrease oxygen uptake by the lungs, and to anoxia. The bronchospasm is the consequence of increased airway smooth muscle cells (ASMC) contraction in response to agonist-mediated receptor stimulation. ASMC contraction is a $Ca^{2+}$-regulated phenomenon which depends in part on voltage-dependent $Ca^{2+}$ channel activity and extracellular $Ca^{2+}$ availability. ASMC contraction can be attenuated by classical $Ca^{2+}$ channel blockers (Soto J, et al., 16:49–52, 1994; Ritchie DM, et al., *Int. Arch. Allerg. Immunol*, 100:274–282, 1993; Dodd JH, et al. *Drug Design & Discovery*, 10:65–75, 1993).

By reducing calcium uptake by ASMC and blocking $Ca^{2+}$ channel activity, retinoid-based calcium channel blockers could prevent bronchospasm and reduce asthma-dependent anoxia.

Gastrointestinal motility is in part dependent on intestinal smooth muscle cell (ISMC) contraction and relaxation. ISMC contraction, similarly to SMC from other tissues is dependent on calcium uptake (Triggle DJ et al., *Ann. NY Acad Sci*. 560:215–229, 1989; Yu J et al. *Gastroenterology*, 100:1448–1460, 1991). $Ca^{2+}$ channel blockers have been shown to experimentally affect (1) esophageal motility (reduce low esophageal sphincter pressure), gastric motility (inhibit gastric emptying), (3) small bowel motility (reduce spontaneous phasic motility in rabbit duodenum), (4), colonic motility (inhibit agonist-induced colon contraction), and (5) Sphincter of Oddi motility (decrease basal sphincter pressure) (De Ponti F. et al., *Pharmac. Ther*., 60:121–148, 1993).

Therefore, retinoids have a potential in the treatment of gastrointestinal disorders secondary to exaggerated motor activity.

It is well established that the uterine smooth muscle (USM) is characterized by a high degree of electrical and contractile activity. It is also established that the availability of extracellular $Ca^{2+}$ (or the presence of blockers of $Ca^{2+}$ channels) strongly influences the response to uterine smooth muscle to various stimuli. Premature births account for a large fraction of perinatal morbidity and mortality. Despite major advances in neonatal care, retention of the fetus in utero is preferred in most instances.

Retinoids and analogues could thus be used as agents that inhibit uterine contraction. Indications would be (1) delay or prevent premature parturition, and (2) slow or arrest delivery for brief periods in order to undertake other therapeutic measures.

Disturbances in calcium homeostasis are also associated with various forms of cataracts. Cataract is a lens disease which leads to blindness and is often seen in diabetic patients. Experimental studies have shown that calcium channel blockers can reduce the incidence of cataracts in diabetes (Pierce, et al. (1989) *Endocrinology*, 125(2): 730–735) and prevents calcium-induced cataract-like lens degenerescence in vitro (Bhatnagar, et al. (1995) *Exp. Eye Res.*, 61(3): 303–310). Therefore, by reducing calcium uptake in the lens, retinoids could be used in the treatment of various forms of cataracts.

II. Retinoids and Their Preparation.

As indicated above, it was a discovery of this invention that retinoids act as potent calcium channel blockers and act to prevent calcium influx into a cell. The IUPAC-IUB Joint Commission on Biochemical Nomenclature states that "retinoids are a class of compounds consisting of four isoprenoid units joined in a head to tail manner. All retinoids may be formally derived from a monocyclic parent compound containing five carbon-carbon double bonds and a functional group at the terminus of the acyclic portion. The basic retinoid structure is generally subdivided into three segments, namely the polar terminal end, the conjugated side chain, and the cyclohexenyl ring. The basic structure s of the most common natural retinoids are called retinol, retinaldehyde, and retinoic acid. Preferred retinoids of this invention are illustrated in Formula I:

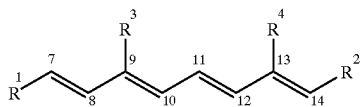

Where $R^1$ is

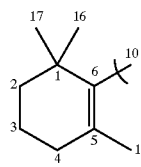

$R^2$ and $R^3$ are independent and include $CH_3$, $CH_2OH$, $CHO$, $CH_2CH_3$, and CF3. In a particularly preferred embodiment, $R^2$ and $R^3$ are $CH_3$. $R^2$ includes $CH_2OH$, $CHO$, $COOH$, $CH_2OH$, $CH_2OCH_3$, $CH_2OC_4H_9$, $CH_2OC_6H_5$, $CH_2OC_8$, $H_{17}$, providing all-trans- (and cis)-retinyl ethers, $R^2$ includes $CH_2OCOCH_3$ or $COC_{15}H_{31}$, providing all-trans- (and cis)-retinyl esters, $R^2$ includes $CH_2NHCOCH_3$, $CH_2NHCOC_6H_5$, $CH_2NCH_3COCH_3$, $CH3COC_6H_5$, providing all-trans- (and cis)- retinylamine derivatives, $R^2$ includes $CH=O$, $CH=NOH$, $CH=NNHCOCH_3$, $CH=C(COCH_2CH_2CH_3)_2$, $CH=C(COCH_2)_2$, $CH=C(COCH_2)_2CH_2CH=C(COCH_2CH_2)_2CH_2$, providing all-trans- (and cis)-retinal derivatives, $R^2$ includes $COOH$, $COOCH_3$, $COOCH_2H_5$ (providing all-trans- (and cis)-retinoic acid esters), $R^2$ includes $COR^5$ where $R^5$ is an amino acid such as glycine, leucine, phenalanine, or tyrosine thereby providing an all-trans- (and cis)-retinoylamino acid, $R^2$ includes $CONHC_2H_5$, $CONHC_3H_7$, $CONH_2$—$C_2H_4OH$, $CONH_2$—$C_3H_6OH$, $CONH_3$—$C_3H_6OH$, $CONHC_6H_5$, $CONH_2$—$C_6H_4OH$, $CONH_4$—$C_6H_4OH$, $CONH_2$—$C_6H_4COOH$, $CONH_4$—$C_6H_4$—$COOH$ (providing all-trans- (and cis)-retinamides). Retinoids thus, include side-chain modified cis and multi-cis retinoids such as, but not limited to, 13-cis-retinoic acid derivatives such as 13-cis-retinoic acid, N-ethyl-13-cis-retinamide, N-(2-hydroxyethyl)-13-cis-retinamide, N-(4-hydroxyphenyl)-13-cis-retinamide, N-(13-cis-retinoyl(leucine), and N-(13-cis-retinoyl)phenylalanine, bifunctional retinoic acid analogs such as 14-carboxyretinoic acid, ethyl 14-(ethoxycarbonyl) retinoate, and 14-[(ethylamino) carbonyl] -13-cis-retinoic acid. Retinoids also include ring-modified analogues such as the ring-modified all-trans-retinoic acid analogues including but not limited to α-retinoic acid, 4-hydroxyretinoic acid, phenyl analogue of retinoic acid, 4-methoxy-2,3,6-trimethylphenyl analogue of retinoic acid, 5,6-dihydroretinoic acid, 4-oxoretinoic acid, 3-pyridyl analogue of retinoic acid, dimethylacetylcyclopentenyl analogue of retinoic acid, 2-furyl analogue of retinoic acid, and the 3-thienyl analogue of retinoic acid. Ring-modified retinoids also include retinoid analogues in which the cyclohexenyl ring is replaced by naphtoquinone-related structures.

Retinoids also include side-chain modified all-trans-retinoic acid analogues such as a $C_{15}$ analogue of retinoic acid, a $C_{17}$ analogue of retinoic acid, a $C_{22}$ analogue of retinoic acid, an aryltriene analogue of retinoic acid, 7,8-dihydroretinoic acid, 8,10-dihydroretinoic acid, 11,12-dihydroretinoic acid. Other side chain modified retinoids include retinol, retinoic acid, and other retinoids with a partially or completely hydrogenated side chain. Still other retinoids having modified side chain include, but are not limited to, retinol or retinoic acid derivatives in which selected double bonds of the side chain are replaced with amide, sulfonamide, or other groups such as, but not limited to, p-(5,6,7,8-tetrahydro-15 5,5,8,8-tetramethyl-2-haphtalene-carboxamido)benzoic acid.

Other retinoids include both ring- and side-chain-modified analogs of all-trans-retinoic acid including, but not limited to (E)-4-[2-(5,6,7,8-tetrahydro-5,5,8, 8-tetramethyl-2-naphthalenyl)-1-propenyl]benzoic acid, (E)-4-[2-( 5,6,7, 8-tetrahydro-8, 8-dimethyl-2-naphthalenyl)-1-propenyl] benzoic acid, (E)-4-[2-( 5,6,7,8-tetrahydro-5,5,8, 8-tetramethyl-2-naphthalenyl)carbamolyl] benzoic acid, (E)-4-[2-( 5,6,7,8-tetrahydro-5,5,8, 8-tetramethyl-2-naphthalenyl)carboxamido]benzoic acid, (E)-4-[2-( 2,3-dihydro-1,1,2,3, 3-pentamethyl-1H-inden-5-yl)-1-propenyl] benzoic acid, 6-( 5,6,7,8-tetrahydro-5,5,8, 8-tetramethyl-2-naphthalenyl)-2-naphthalenecarboxylic acid, 6-( 5,6,7,8-tetrahydro-5,5,8, 8-tetramethyl-2-naphthalenyl)-5-methyl-2-naphthalenecarboxylic acid, 6-(5,6,7, 8-tetrahydro-5,5,8, 8-tetramethyl-2-naphthalenyl)-6-benzo[b] thiophenecarboxylic acid, 4-(5,6,7, 8-tetrahydro-5,5,8,8-tetramethyl-2-anthracenyl)benzoic acid, and (E)-4-[3-( 3,5-Di-tert-butylphenyl)-3-oxo-1-propenyl]benzoic acid. Detailed descriptions of these and other retinoids can be found in Brahama et al. (1990) *Meth. In Enzymology*, 189: 43–59, Klaus et al. (1990) *Meth. In Enzymology*, 189: 3–14, Dawson et al. (l990) *Meth. In Enzymology*, 189: 15–42. Other preferred retinoids include glucuronic acid, retinyl β-glucuronide, and retinoyl β-glucuronide. In a particularly preferred embodiment, the retinoid is retinol (Formula III).

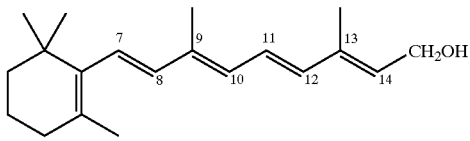

III

A large number of retinoids are commercially available (e.g., from Sigma Chemical Co., St. Louis, Mo. or from Aldrich Chemical Co., Inc., Milwaukee, Wis., etc.). In addition, means of synthesizing and/or purifying retinoids are well known to those of skill in the art (see, e.g., Brahama et al. (1990) Meth. In Enzymology, 189: 43–59, Klaus et al. (1990) Meth. In Enzymology, 189: 3–14, Dawson et al. (1990) Meth. In Enzymology, 189:15–42; U.S. Pat. Nos: 5,648,091, 5,637,779, 5,639,919, 5,426,247, 4,876,400, and Kirk-Othmer, (1978) Encyclopedia of Chemical Technology, 24: 140).

III. Retinoid Administration.
A) Direct and Indirect Application.

In the methods of this invention, the retinoids can be administered either directly or indirectly. Direct administration refers to the administration of an exogenous retinoid to the subject organism as described below. Retinoids, however, occur endogenously in mammalian cells and in biological fluids such as blood, plasma, lymph, and endogenous retinoid concentration can be increased by the administration of compounds that block or upregulate various components in the retinoid metabolic pathway. Thus, for example, intracellular retinol levels can be increased by administration of compounds that inhibit the conversion of retinol to retinoic acid. Citral, for example, has been shown to inhibit the conversion of retinol into retinoic acid (Hebuterne et al. (1996) J. Lipid Res., 37: 482–492; Tanaka (1996) Development. Biol., 175: 239–247). Citral or related analogues could thus induce accumulation and reinforce the activity of retinol. Alternatively, or in addition, retinoid precursors such as but not limited to β-carotene, can increase endogenous concentrations of retinoids (Scita et al. (1993) Methods in Enzymol., 214: 21–32). The use of such methods to increase the levels of or more endogenous retinoids may be regarded as "indirect retinoid administration".

D) Dosates and Schedules

An effective (therapeutically effective) quantity of retinoid is employed in treatment. The dosage of compounds used in accordance with this invention varies depending on the compound and the condition being treated.

The age, weight, and clinical condition of the recipient patient; and the experience and judgment of the clinician, practitioner, or veterinarian administering the therapy are among the factors affecting the selected dosage. Other factors include the route of administration the patient, the patient's medical history, the severity of the disease process, and the potency of the particular compound. The dose should be sufficient to ameliorate symptoms or signs of the disease or to provide effective prophylaxis without producing unacceptable toxicity to the patient.

Broadly, a dosing schedule is from about 2 mg to about 2000 mg two or three times a day. More typically, a dose is about 20mg to about 400 mg of compound given three times a day. A convenient oral dose for an adult patient is 30 mg three times a day (e.g. after meals).

A dosage range for topical treatment (e.g., in the treatment of intraocular hypertension) is about 0.1% to about 10% (weight/volume) in a physiologically acceptable eye drop applied one to five or even ten times a day. A usual dose for intra-articular injection is 20–40 mg injected per joint, not generally exceeding three joints per therapy session. A typical dosage for intra-dermal administration is about 20–75 mg per injection per site. It will be appreciated that such dosages are typically advisorial in nature and may be adjusted depending on the particular therapeutic context, patient tolerance, etc. Substantially higher dosages are possible by any selected route, for example, topical administration.

Typically, the dosage is administered at least once a day until a therapeutic or prophylactic result is achieved. Preferably, the dosage is administered twice a day, but more or less frequent dosing can be recommended by the clinician. Once a therapeutic result is achieved, the drug level can be modified for maintenance treatment. Under some conditions, the drug may be tapered or discontinued after the appearance of a therapeutic result. Occasionally, side effects warrant discontinuation of therapy. In general, an effective amount of the compound is that which provides either subjective relief of symptoms or an objectively identifiable improvement as noted by the clinician or other qualified observer.

E) Pharmaceutical Compositions

The retinoids of this invention can be administered orally, transdermally, by subcutaneous or other (e.g., intravenous or intra-arterial) injection, intravenously, topically, parenterally, transdermally, rectally or via by sustained release methods, e.g., an implanted reservoir containing retinoid composition. In the case of opthamlic formulations, the retinoid composition is preferably applied topically (e.g., in eye drops).

The form in which the retinoid will be administered (e.g., powder, tablet, capsule, solution, emulsion) will depend on the route by which it is administered. The quantity of the drug to be administered will be determined on an individual basis, and will be based at least in part on consideration of the individual's size, the severity of the symptoms to be treated and the result sought as described above.

The retinoid compounds are preferably administered in the form of an acid addition salt thereof, concurrently, simultaneously, or together with a pharmaceutically-acceptable carrier or diluent, especially and preferably in the form of a pharmaceutical composition thereof, whether by the topical, oral, rectal, or parenteral (including subcutaneous) route, in an effective amount.

The compositions for administration will commonly comprise a solution of the retinoid dissolved or suspended in a pharmaceutically acceptable carrier, preferably a lipid or lipid compatible carrier for lipid soluble retinoids. A variety of carriers can be used, e.g. buffered saline containing suitable emulsifiers, and the like.

Pharmaceutically acceptable carriers (excipients) can contain a physiologically acceptable compound that acts, for example, to stabilize the composition, and/or to increase or decrease the absorption of the agent. Physiologically acceptable compounds can include, for example, carbohydrates, such as glucose, sucrose, or dextrans, antioxidants, such as ascorbic acid or glutathione, chelating agents, low and/or high molecular weight proteins, compositions that reduce the clearance or hydrolysis of the retinoid(s), or excipients or other stabilizers and/or buffers. Other physiologically acceptable compounds include wetting agents, emulsifying agents, dispersing agents or preservatives which are particularly useful for preventing the growth or action of microorganisms.

Because most retinoids are lipid soluble the use of solubilizers and/or emulsifiers is often desired to produce aqueous retinoid solutions or emulsions. Such solubilizers and emulsifiers are well known to those of skill in the art.

For example, lower alkyl alcohols having from 2 to 3 carbon atoms are useful as diluents or solvents for retinoids in the preparation of stabilized retinoid compositions of the invention. Particularly useful alcohols are selected from the group consisting of ethyl alcohol, n-propyl alcohol and mixtures thereof These alcohols are useful generally in the proportions by weight of about 1 to about 25 percent, preferably about 3 to about 15 percent, more preferably about 4 to about 10 percent, and most preferably about 4 to about 6 percent by weight, all based upon the weight of the retinoid. These alcohols are miscible in both water and many oils and can, therefore, be utilized as solvents for most of the forms of the fat-soluble retinoids. These alcohols also serve to control the viscosity of the retinoid composition and act as secondary emulsifiers. Additionally, the alcohols can act as freeze depressants maintaining the fluidity of the retinoid composition at lower temperatures.

The emulsifier system optionally utilized in the retinoid compositions of this invention can be selected from the various nonionic emulsifiers. The emulsifiers used must be acceptable as additives for oral administration and/or for intravenous administration and have no significant deleterious effect upon the retinoid used therewith or upon the effectiveness of the lower alkyl alcohol utilized as a solvent or diluent. Generally, the emulsifier system should have a hydrophilic-lipophilic balance (HLB) suitable to provide self-emulsification properties to the retinoid containing composition. The HLB of the emulsifier system should be about 3 to about 17, preferably about 5 to about 14, and most preferably about 10. to about 14. Generally, most nonionic emulsifiers or mixtures of nonionic emulsifiers will meet these criteria. The proportion by weight of emulsifier utilized in the retinoid containing compositions of the invention is generally about 25 percent to about 60 percent, preferably about 35percent to about 55 percent, and most preferably about 40 percent to about 50 percent, all based upon the weight of said emulsifiable concentrates. A practical emulsifier system must have an adequate balance between the oil emulsified and the water in which the emulsification takes place. The required HLB will decrease as the oil phase becomes less hydrophilic, for instance, as the carbon number of a straight chain alcohol increases. Generally, an HLB range will provide satisfactory results, however, this range will narrow as the oil and water phases become more widely separated in properties.

The following specific examples of food grade emulsifiers are useful in the orally administered retinoid compositions of the invention: sorbitan monostearate, polyoxyethylene glycol monooleate, polyoxyethylene glycol dioleate, polyethylene glycol mono- and dioleate, mono- and diglycerides of animal fats, monoglycerides of coconut oil, monoglycerides of peanut oil, and propylene glycol.

Because of the sensitivity to chemical deterioration of many retinoids, it is helpful to incorporate an antioxidant in the pharmacological composition. One of the useful antioxidants known in the art which can be used herein is termed ethoxyquin which is otherwise known as 6-ethoxy-1,2-dihydro-2,2,4-trimethylquinolin. The use of such an antioxidant lengthens the shelf life and minimizes the chemical deterioration and degradation retinoids. Without being bound to a particular theory, it is believed that the ethoxyquin is preferentially oxidized in solution and thereby protects the fat-soluble retinoids from chemical deterioration and degradation.

The proportions of antioxidants and/or yeast, and mold inhibitors, and preservatives which are useful can be determined by one skilled in the art without extensive testing. Generally, amounts less than about 10 to about 20 percent by weight based upon the weight of the compositions can be used. The proportion of various diluents, aritioxidants and other preservatives may be limited by the present requirements of the Food and Drug Administration.

The retinoid based pharmacological compositions are preferably sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component. In, tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

It is recognized that the retinoids, when administered orally, must be protected from digestion. This is typically accomplished either by complexing the retinoid with a composition to render it resistant to acidic and enzymatic hydrolysis or by packaging the retinoid in an appropriately resistant carrier such as a liposome. Means of protecting compounds from digestion are well known in the art (see, e.g., U.S. Pat. No. 5,391,377 describing lipid compositions for oral delivery of therapeutic agents)

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For example, parenteral injection liquid preparations can be formulated in solutions in aqueous polyethylene glycol solution.

Aqueous solutions suitable for oral use can be prepared by dissolving the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, and other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

In the treatment or prophylaxis of opthalmic disorders, topical ophthalmic preparations, for example ocular drops, gels or creams, are preferred because of ease of application, ease of dose delivery and fewer systemic side effects, such as cardiovascular hypotention. Topical ophthalmic formulations are well known to those of skill in the art and can be found, for example, in U.S. Pat. No. 5,435,998.

The concentration of retinoids or other active ingredients in these formulations can vary widely, and will be selected primarily based on fluid volumes, viscosities, body weight and the like in accordance with the particular mode of administration selected and the patient's needs.

D) Multiple Therapeutic Combinations.

In the method of the present invention, the retinoid formulation can be administered along with one or more additional drugs. For example, other anti-hypertensive agents, such as thiazide-type diuretics and beta blockers, can be given with or in close temporal proximity to administration of the retinoid.

Calcium channel blockers, by limiting the uptake of calcium in vascular smooth muscle, are beneficial, but have been found to stimulate some endocrine systems, such as the renin-angiotensin system (RAS) (Kotchen et al. (1988) *Am. J. Cardiol.*, 62: 41G Matsumara et al. (1978) *J. Pharmacol Exp. Ther.*, 241: 1000; Resnick et al. (1986) *Fed Proc.*, 45: 2739). Utilization of calcium channel blockers may be limited by excessive vasodilation, negative inotropy, excessive depression of the sinus nodal rate, atrial-ventricular nodal conduction disturbances and interference with non-vascular smooth muscle contraction. It has been discovered that the use of supplemental dietary calcium and calcium channel blockers in combination is an effective method of treatment for hypertension and that the combination therapy employing both agents is more effective and predictable than the use of either agent alone (see, e.g., U.S. Pat. No: 5,350,771). The effect is greater than the sum of the effects of both agents separately. Alternatively, the administration of compounds which are an effective form of Vitamin D, such as 1 alpha, 25-dihydroxycholecalciferol (1,25-(OH)$_2$D$_3$), which increases intestinal calcium absorption, together with a retinoid calcium channel blocker is a convenient treatment modality.

The two (or more) drugs (retinoid and another drug) can be administered in one composition or as two separate entities. For example, they can be administered in a single capsule, tablet, powder, liquid, etc. or as individual compounds. The components included in a particular composition, in addition to the retinoid, and another drug or drugs, are determined primarily by the manner in which the composition is to be administered. For example, a composition to be administered orally in tablet form can include, in addition to the drugs, a filler (e.g., lactose), a binder (e.g., carboxymethyl cellulose, gum arabic, gelatin), an adjuvant, a flavoring agent, a coloring agent and a coating material (e.g., wax or a plasticizer) as described above. A composition to be administered in liquid form can include the combination of drugs and, optionally, an emulsifying agent, a flavoring agent and/or a coloring agent as described above.

IV. Kits

In another embodiment, this invention provides kits for the practice of the methods of this invention. The kits preferably include one or more containers containing a retinoid and a pharmaceutically acceptable excipient. The kit may optionally contain additional therapeutics to be co-administered with the retinoid.

The kits may also optionally include appropriate systems (e.g. opaque containers) or stabilizers (e.g. antioxidants) to prevent degradation of the retinoids by light or other adverse conditions.

The kits may optionally include instructional materials containing directions (i. e., protocols) providing for the use of a retinoid in the treatment of a disease in a mammal wherein the disease is characterized by a symptom ameliorated by inhibition of cellular calcium influx. In particular the disease can include any one or more of the disorders described herein including, but not limited to hypertension (end stage renal hypertension, pregnancy-related hypertension (e.g., preeclampsia), salt sensitivity hypertension, type II diabetes hypertension, alcohol abuse or obesity related hypertension, systolic hypertension in the elderly, and essential hypertension), ischemic and hemorrhagic stroke, vascular dementia, asthma, allergies, migraine headache, gastrointestinal motility disorders, Alzheimer's disease, senile dementia, angina pectoris, premature labor, convulsive epilipsy, and alcohol withdrawal.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following example is offered to illustrate, but not to limit the present invention.

Example 1

A) Retinol Inhibition of KCl Induced Vascular Contractions.

Rat mesenteric arteries were mounted in a wire myograph, bathed in a physiological solution, and incubated for 5 min. with either retinol (10 $\mu$M, open diamonds) or its vehicle (ethanol, 0.1% v/v, closed circles). KCl was then added to the preparation at various concentrations, and the contractile response was measured. Results are presented in FIG. 1 as active stress (force/unit of length; mN/mm) plotted against KCl concentrations (mM). The asterisks indicate a significant difference in the response to KCl for retinol-treated arteries vs. vehicle-treated arteries.

B) The Inhibitory Effect of Retinol on Vascular Contractions Induced by Noreninephrine.

Figure 2:
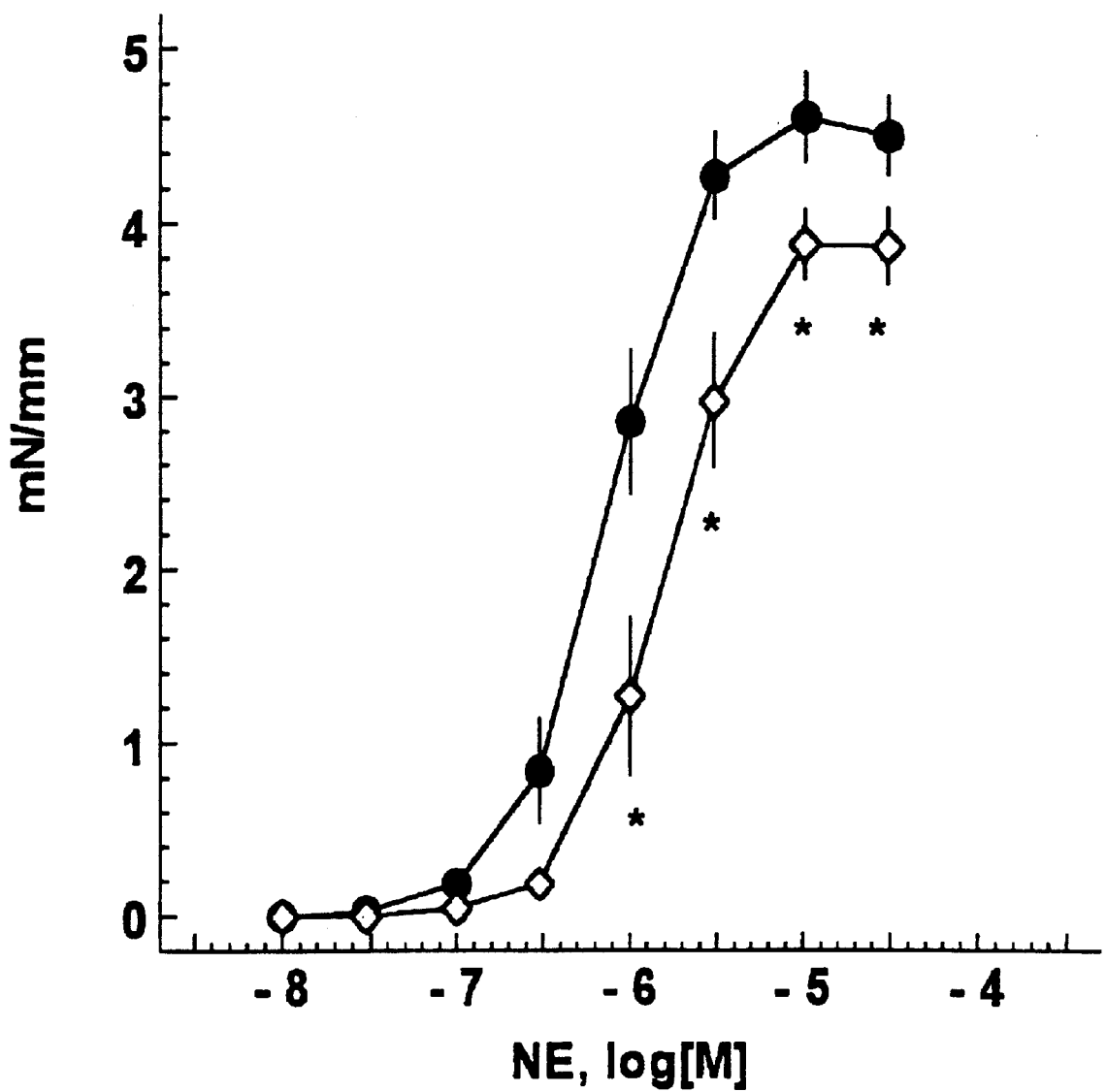
FIG. 2 shows the inhibitory effect of retinol on vascular contractions induced by norepinephrine.

In this experiment, rat mesenteric arteries were mounted in a wire myograph, bathed in a physiological solution, and incubated for 5 min. with either retinol (10 $\mu$M, open diamonds) or its vehicle (ethanol, 0.1% v/v, closed circles). Norepinephrine (NE) was then added to the preparation at various concentrations, and the contractile response was measured. The results, shown in FIG. 2, are presented as active stress (force/unit of length; mN/mm) plotted against NE concentrations (M). The asterisks indicate a significant difference in the response to NE for retinol-treated arteries vs. vehicle-treated arteries.

C) The Inhibitory Effect of Retinol on Vascular Smooth Muscle, Voltage-Dependent $Ca^{2+}$ Sionaling.

Figure 3:
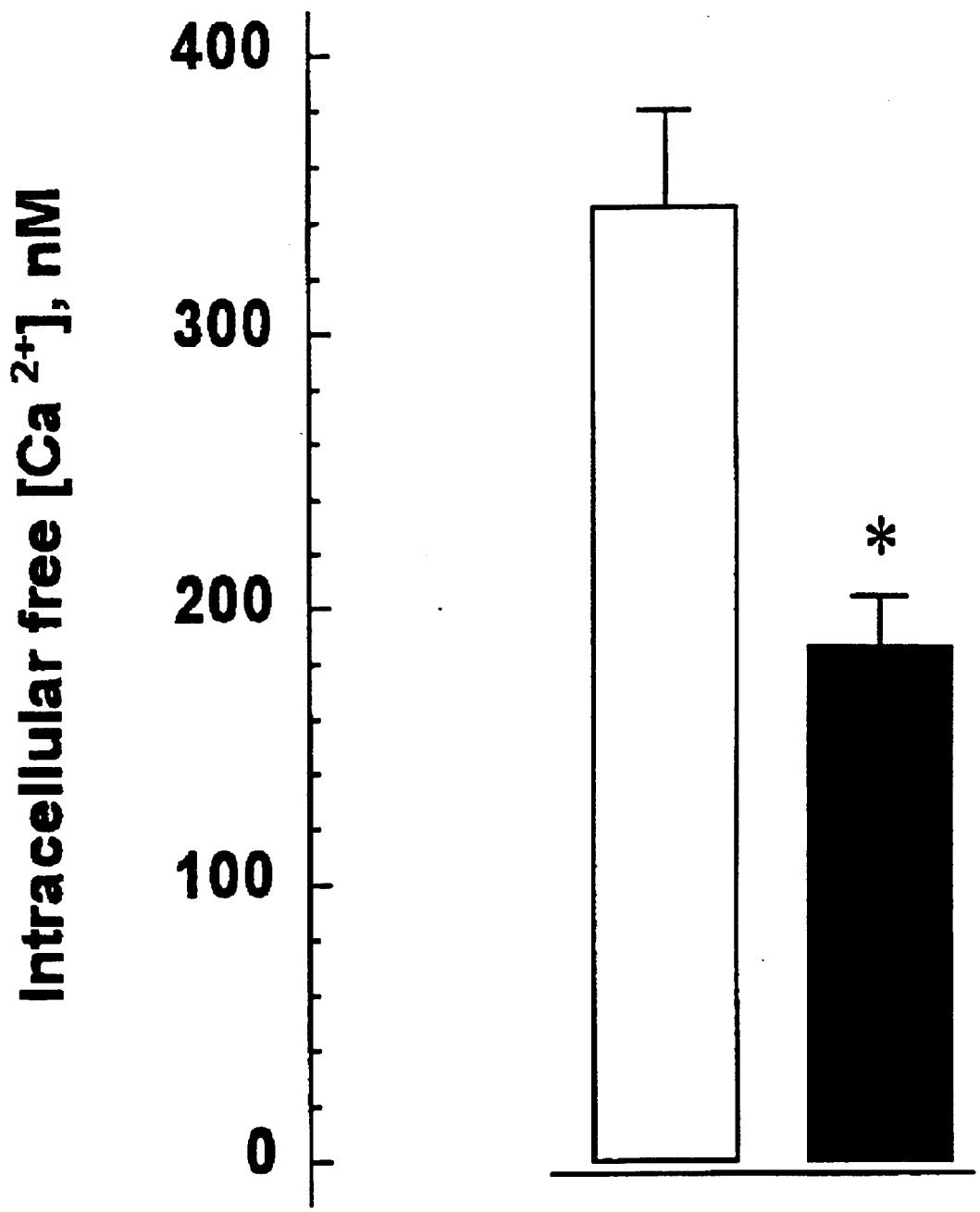
FIG. 3 is a bar graph showing the inhibitory effect of retinol on vascular smooth muscle, voltage-dependent $Ca^{2+}$ signaling.

Rat mesenteric arteries were mounted in a wire myograph, bathed in a physiological solution, and incubated with fura 2/AM, a $Ca^{2+}$-sensitive fluorescent indicator. The arteries were then positioned under a microscope connected to a spectofluorometer. Fluorescence measurements representing intracellular free $Ca^{2+}$ concentrations ($[Ca^{2+}]$ in nM) were performed before (resting) and after stimulation of contraction with a high (100 mM) depolarizing concentration of NE. The results are show in FIG. 3. The light bar represents control $[Ca^{2+}]$ response; the dark bar represents the $[Ca^{2+}]$ response after treatment with retinol (10 $\mu$M, 15-min exposure). A statistically significant difference is noted with "*".

D) Retinol Does Not Affect $Ca^{2+}$-Induced Vascular Smooth Muscle Contraction.

Figure 4:
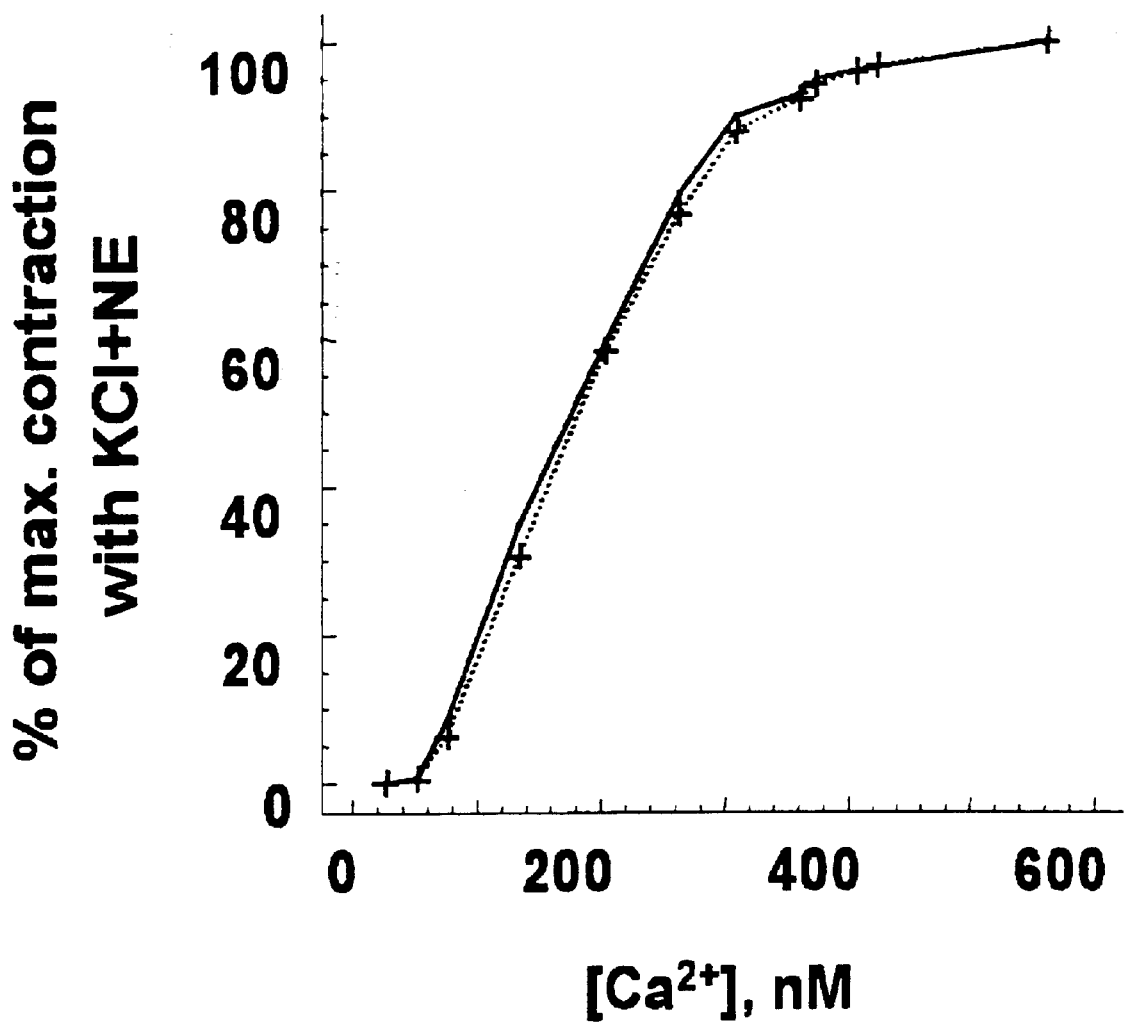
FIG. 4 is a plot which shows that retinol does not affect $Ca^{2+}$-induced vascular smooth muscle contraction.

In these experiments, rat arteries were mounted in a wire myograph and permeabilized with Staphylococcus Aureus a-toxin. Contraction (expressed as % of contraction obtained with 100 mM KCl and $10^{-6}$ M norepinephrine (NE) before α-toxin permeabilization) was initiated with $Ca^{2+}$ at the concentrations indicated in FIG. 4. The solid line represents control arteries; while the dotted line represents arteries treated with 25 $\mu$M retinol for 30 min.). In α-toxin permeabilized arteries, $Ca^{2+}$ goes freely across smooth muscle cell plasma membrane, thus bypassing the regulation of $Ca^{2+}$ influx by voltage-dependent $Ca^{2+}$ channels. However, $Ca^{2+}$-sensitive pathways responsible for smooth muscle contraction are intact and constriction can be triggered by increasing extracellular $Ca^{2+}$ concentration. These experiments suggest that retinol affects exclusively smooth cellular $Ca^{2+}$ influx.

E) The Inhibitory Effect of Retinoic Acid (RA) on Vascular Contractions Induced by KCl.

Figure 5:
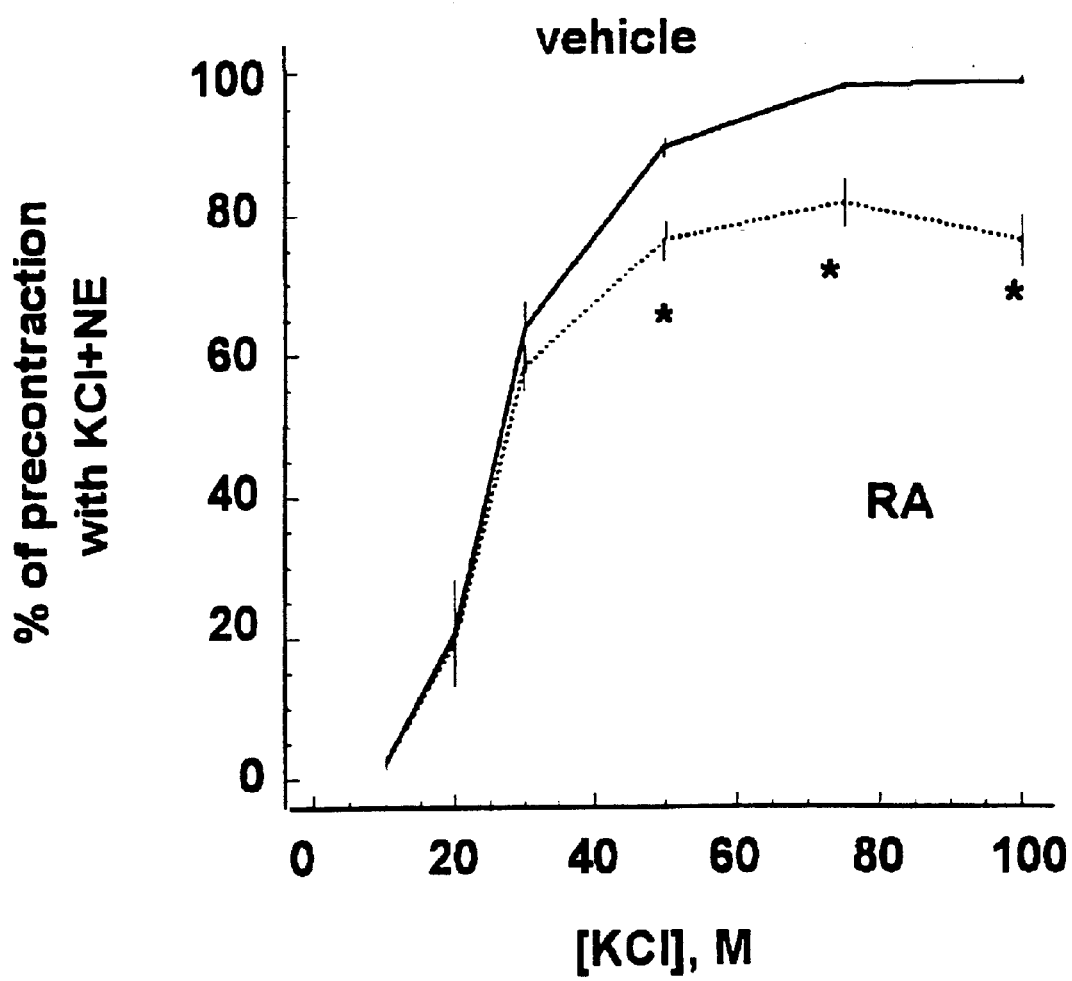
FIG. 5 is a plot showing the inhibitory effect of retinoic acid (RA) on vascular contractions induced by KCl.

In this experiment, human arteries (~200 $\mu$m diameter, 2–3 mm long) were mounted in a wire myograph, bathed in a physiological solution, and incubated for 10 min. with either retinoic acid (RA) (10 $\mu$M, dotted line in FIG. 5) or vehicle (ethanol, 0.1% v/v, solid line). KCl was then added to the preparation at various concentrations, and the contractile response was measured. The results, shown in FIG. 5, are presented as contraction (in % of the contraction obtained with 100 mM and $10^{-5}$ M norepinephrine (NE) in the absence of vehicle or RA) plotted against KCl concentrations (mM). Significant differences in the response to KCl are noted with "*".

F) The Inhibitory Effect of Retinoic Acid on Vascular Contractions Induced by Norevinephrine.

Figure 6:
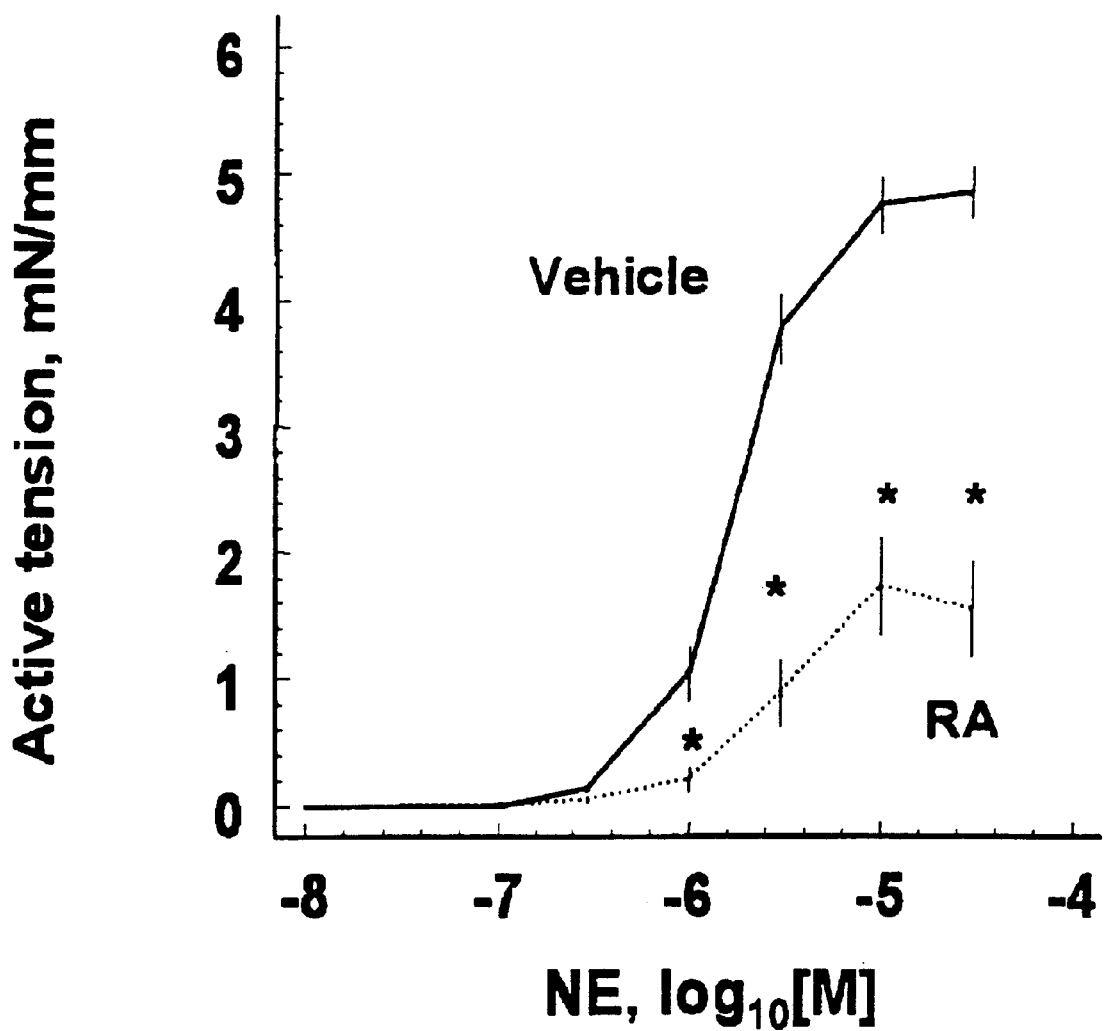
FIG. 6 is a plot showing the inhibitory effect of retinoic acid on vascular contractions induced by norepinephrine (NE), a neurotransmitter with vasoconstrictor properties.

In this experiment, rat mesenteric arteries were mounted in a wire myograph, bathed in a physiological solution, and incubated for 5 min. with either retinoic acid (10 $\mu$M, dotted line in FIG. 6) or vehicle (ethanol, 0.1% v/v, solid line). NE was then added to the preparation at various concentrations, and the contractile response was measured. The results, shown in FIG. 6, are presented as active stress (force/unit of length; mN/mm) plotted against NE concentrations (M). Asterisks indicate a significant difference in the response to KCl for retinoic acid (RA)-treated arteries vs. vehicle-treated arteries.

G) The Inhibitory Effect of Retinol on $Ca^{2+}$ Currents.

Figure 7:
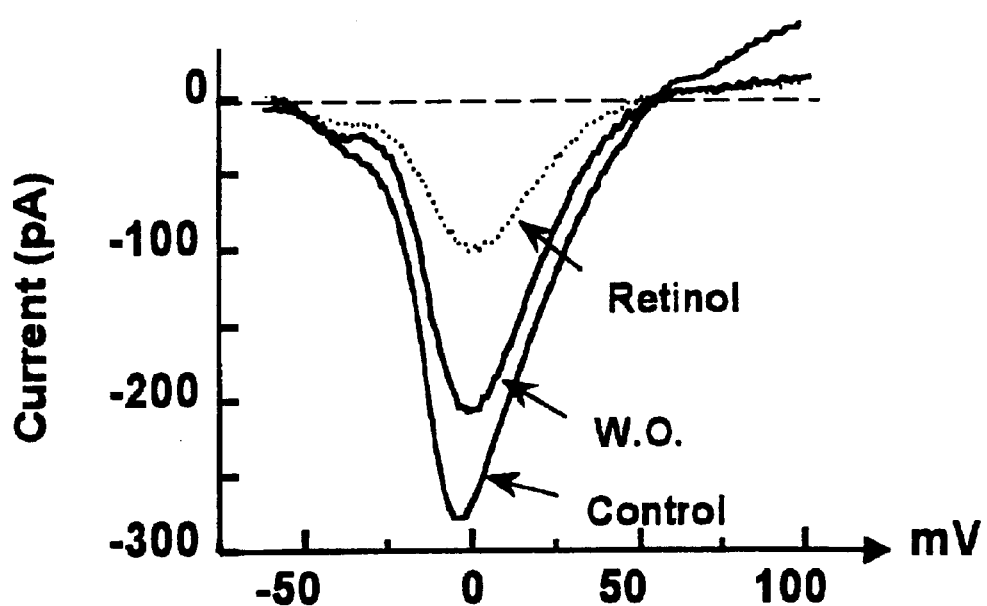
FIG. 7 shows the inhibitory effect of retinol on $Ca^{2+}$ currents.
Figure 7:
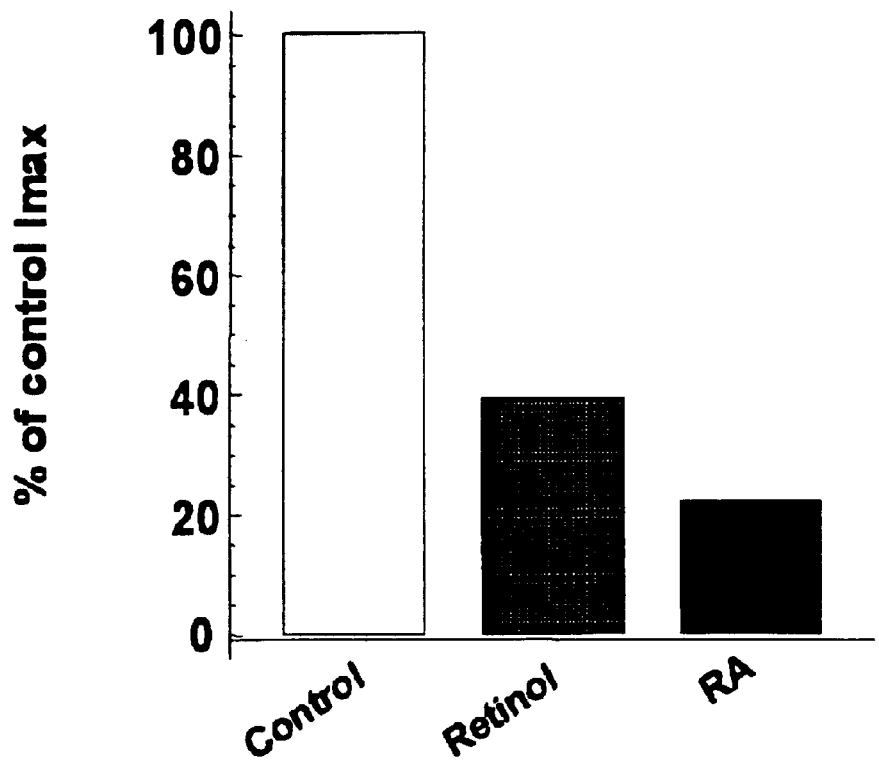

In these experiments, a recording pipette filled with appropriate buffer solution was applied at the surface of a single smooth muscle cell while voltage was controlled electronically. When voltage was varied from –100 mV to +100 mV, an inward (negative) current corresponding to the opening of plasma membrane L-type $Ca^{2+}$ channels was observed. In control conditions (solid line in FIG. 7, panel A) this current starts to increase frankly around –25 mV, is maximum around 0 mV (maximum intensity, Imax), and inactivates around +50 mV. Retinol (10 $\mu$M, dotted line, panel A) inhibited voltage-dependent $Ca^{2+}$ channel opening. In the experiment shown in panel A, the effect of retinol was reversible. FIG. 7, panel B shows the effect of retinol (10 $\mu$M, gray bar) and RA (10$\mu$M, dark bar) on Imax as % of control Imax (100 %, light bar).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference.

What is claimed is:

1. A method for treating stroke in a mammal comprising the step of administering to the mammal an effective amount of a retinoid and a pharmaceutically acceptable excipient wherein the amount of administered retinoid is from about 20 mg to about 400 mg and the amount is administered from two to three times per day.

2. The method of claim 1, wherein said retinoid is retinol.

3. The method of claim 2, wherein said retinoid is retinoic acid.

4. The method of claim 2, wherein said mammal is a human.

5. The method of claim 2, wherein said pharmacologically acceptable excipient is lipid compatible.

6. The method of claim 2 further comprising assaying said mammal for amelioration of a symptom of said stroke wherein said symptom is expected to be responsive to treatment with said retinoid.

\* \* \* \* \*